United States Patent [19]

Smith et al.

[11] Patent Number: 4,835,140
[45] Date of Patent: May 30, 1989

[54] METHOD FOR TREATING PNEUMOCYSTIS CARINII PNEUMONIA PATIENTS WITH CLINDAMYCIN AND PRIMAQUINE

[75] Inventors: James W. Smith; Marilyn S. Bartlett; Sherry F. Queener, all of Indianapolis, Ind.

[73] Assignee: Indiana University Foundation, Bloomington, Ind.

[21] Appl. No.: 87,378

[22] Filed: Aug. 20, 1987

[51] Int. Cl.⁴ ..................... A61K 31/70; A61K 31/71
[52] U.S. Cl. ........................................ 514/24; 514/310
[58] Field of Search .................................. 514/24, 310

[56] References Cited

U.S. PATENT DOCUMENTS

| | | | |
|---|---|---|---|
| 3,856,943 | 12/1974 | Birkenmeyer | 514/24 |
| 4,293,547 | 10/1981 | Lewis et al. | 514/24 |
| 4,368,193 | 1/1983 | Argondelts et al. | 514/24 |
| 4,746,651 | 5/1988 | Goodman | 514/45 |

OTHER PUBLICATIONS

*Physicians Desk Reference,* Charles Baker, Jr.; Publisher, 1977, 31st Edition, pp. 1616 and 1701.
Hughes, W. T., et al., Antimicrobial Agents and Chemotherapy 5:289-293 (1974).
Hughes, W. T. and Smith, B. L., Antimicrobial Agents and Chemotherapy 26:436-440 (1984).
Perez, G., et al., Abstracts of Annual Meeting of American Society for Microbiology, 79 (1985).
Schmidt, L. H., Antimicrobial Agents and Chemotherapy 27:151-157 (1985).
Toshida, T., Medical Journal of Hiroshima University, Paper, 385-398.

*Primary Examiner*—Mark L. Bell
*Attorney, Agent, or Firm*—Paul W. Busse; John T. Reynolds

[57] ABSTRACT

The combination of clindamycin and primaquine or pharmaceutical salts thereof is effective in treating patients with Pneumocystis carinii pneumonia.

15 Claims, No Drawings

METHOD FOR TREATING PNEUMOCYSTIS CARINII PNEUMONIA PATIENTS WITH CLINDAMYCIN AND PRIMAQUINE

FIELD OF THE INVENTION

This invention is a novel treatment of patients having *Pneumocystis carinii* pneumonia.

BACKGROUND OF THE INVENTION

Clindamycin and primaquine are drugs that have been used extensively in humans. Clindamycin is an lincosamide antibiotic active against a variety of bacteria including aerobic gram positive cocci, anaerobic gram negative bacilli, anaerobic gram positive non-spore-forming bacilli, and anaerobic and microaerophilic cocci. The preparation of clindamycin is given by Magerlein, et al., in Anti-microbial Agents and Chemotherapy, 727 (1966). Clindamycin also has activity against malarial parasites although the exact effect on plasmodia is not known. The drug is rapidly and virtually completely absorbed after oral dosage and distributes well into body fluids and tissues. Primaquine is a potent anti-malarial agent now used mainly for radical cure of vivax malaria. The preparation of primaquine is given by Elderfield, et al., in Journal of the American Chemical Society, 4816 (1955). The drug is rapidly absorbed after oral dosage and has extensive tissue distribution.

An estimated one to one and one-half million people in the United States are infected with a human retrovirus, the human immunodeficiency virus type I, HIV-1, which is the etiological agent of acquired immunodeficiency syndrome, AIDS, Norman, C., Science, 661-662 (1986). Of those infected, an estimated two hundred and fifty thousands people will develop AIDS in the next five years, Curran, J.W., et al., Science, 1352-1357 (1985). *Pneumocystis carinii* pneumonia is the most common life threatening infection in patients with aids. The infection occurs at least once in as many as eighty percent of AIDS patients and about one third of the total number of episodes of pneumocystis carinii pneumonia are fatal. Fewer than one half of the AIDS patients treated with conventional drugs, either trimethoprim/sulfamethoxazole or pentamidine, are able to complete a full course of therapy because a majority of these patients develop one or more serious adverse reactions such as severe rash, neutropenia, thrombocytopenia, anemia, liver disfunction, renal failure or disturbances in serum glucose, calcium or sodium levels.

INFORMATION DISCLOSURE

The following documents may be material to the examination of this application.

The abstract, Prognostic Factors in *Pneumocystis carinii* Pneumonia (PCP) in AIDS, presented at the 1985 annual meeting of the American Society for Microbiology by Perez, G., et al., discloses treating AIDS patients with trimethoprim sulfa, pentamidine, or combinations of both including concurrent treatment with clindamycin.

The paper, Efficacy of Trimethoprim and Sulfamethoxazole in the Prevention and Treatment of *Pneumocystis carinii* Pneumonia, Anti-microbial Agents and Chemotherapy, 289-293 (1974) by Hughes, W.T., et al., teaches that rifampin and clindamycin, separately or in combination with pentamidine, were ineffective in the prevention and treatment of *Pneumocystis carinii* infection.

The paper, Studies on the Serodiagnosis, Treatment and Prophylaxis for *Pneumocystis carinii* Pneumonia, Med. J. Hiroshima University, 385-398 (1986) by Toshida, T. teaches use of clindamycin alone or clindamycin with sulfamethoxazole was unsuccessful to prevent or treat pneumocystis carinii pneumonia.

The paper, Enhancement of the Curative Activity of Primaquine by Concomitant Administration of Mirincamycin, Antimicrobial Agents and Chemotherapy, 151-157 (1985) by Schmidt, L.H. teaches the curative action of primaquine in malaria is enhanced when used in combination with mirincamycin. Mirincamycin is a lincosamide antibiotic.

SUMMARY OF THE INVENTION

This invention is a method for treating a patient with *Pneumocystis carinii* pneumonia or for preventing an immunosuppressed patient from developing *Pneumocystis carinii* pneumonia which comprises administering an effective amount of clindamycin and primaquine or pharmaceutical salts thereof to the infected or immunosuppressed patient and a pharmaceutical composition given to a patient with *Pneumocystis carinii* pneumonia or an immunosuppressed patient comprising an effective amount of clindamycin and primaquine or pharmaceutical salts thereof.

DETAILED DESCRIPTION OF THE INVENTION

In this document, the term human immunodeficiency virus means human immunodeficiency virus type I, human immunodeficiency virus type II, or strains, apparent to one skilled in the art, which belong to the same viral family and which create similar physiological effects in humans as human immunodeficiency virus types I or II.

In this document, an immunosuppressed patient means a patient with AIDS or other diseases and conditions known to effect a patient's immune system such as lymphoproliferated malignancies, organ transplants, congenital immunodeficiency disorders and certain vascular disorders.

Patients to be treated would be those immunosuppressed patients associated with AIDS or other diseases and conditions known to affect a patient's immune system such as lymphoproliferative malignancies, organ transplants, congenital immunodeficiency disorders and certain vascular disorders; or those patients having *Pneumocystis carinii* pneumonia proven by open lung biopsy, transbronchial lung biopsy, or bronchial lavage.

Clindamycin and primaquine can be used and administered as pharmaceutical salts. Examples of these salts include the hydrochloride, the hydrobromide, the sulfate or the phosphate hydrate salts of clindamycin and primaquine.

Those skilled in the art would know how to formulate clindamycin and primaquine or pharmaceutical salts thereof into appropriate pharmaceutical dosage forms, either as separate dosage forms or as a single pharmaceutical composition. Examples of the dosage forms include oral formulations, such as tablets or capsules, or parenteral formulations, such as sterile solutions.

When clindamycin and primaquine or salts thereof are administered orally, an effective amount of each drug is from about 0.1 to 100 mg per kg per day. A typical unit dose for a 70 kg human would be from about 30 mg to 500 mg taken one to four times per day. The preferred dosage is 450 mg of clindamycin taken three times a day and 30 mg of primaquine taken once a day. Either solid or fluid dosage forms can be prepared for oral administration. Solid compositions are prepared by mixing clindamycin and primaquine or salts thereof with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing clindamycin and primaquine or salts thereof with an inert pharmaceutical diluent and placing the mixture into an appropriately sized hard gelatin capsule. Soft gelatin capsules are prepared by machine encapsulation of a slurry of clindamycin and primaquine or salts thereof with an acceptable inert oil such as vegetable oil or light liquid petrolatum. Syrups are prepared by dissolving clindamycin and primaquine or salts thereof in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When clindamycin and primaquine or salts thereof are administered parenterally, it can be given by injection or by intravenous infusion. An effective amount is from about 0.1 to 100 mg per kg per day. Parenteral solutions are prepared by dissolving clindamycin and primaquine or salts thereof in water and filter sterilizing the solution before placing in a suitable sealable vial or ampule. Parenteral suspensions are prepared in substantially the same way except a sterile suspension vehicle is used and the clindamycin and primaquine or salts thereof are sterilized with ethylene oxide or suitable gas before it is suspended in the vehicle.

The exact route of administration, dose, or frequency of administration would be readily determined by those skilled in the art and is dependant on the age, weight, general physical condition, or other clinical symptoms specific to the patient to be treated.

The utility of this invention is demonstrated by the ability of clindamycin and primaquine to prevent growth of *Pneumocystis carinii* in culture and to prevent infection in an animal model of *Pneumocystis carinii* pneumonia. In culture, clindamycin alone at concentrations up to 5 ug/ml had no effect; primaquine alone at 50 ug/ml had an effect. In combination at these same doses, clindamycin and primaquine strongly inhibited growth of *Pneumocystis carinii*. Rats immune suppressed with cortisol acetate for eight weeks normally develop *Pneumocystis carinii* infections and are used as a model of *Pneumocystis carinii* pneumonia. In the current study, 10 of 10 control animals developed *Pneumocystis carinii* infections with all animals scoring above 2 on a scale for infection from 0 to 4. Clindamycin prophylaxis, 5 mg/kg daily, during the immune suppression did not prevent infection, 7/7 had infectivity scores above 3. Primaquine alone, 0.5 mg/kg daily, during immune suppression reduced the severity of infection, 0.5 to 1.7 scores, but 7 of 8 animals were infected. In contrast, the combination of clindamycin and primaquine prevented infection in 8 of 10 animals; the other two animals had scores of 0.2 and 0.3. Cortisol concentrations at the time of sacrifice were not significantly different for the groups. Hematology did not reveal significant toxicity in the animals treated with the combination.

Without further elaboration, those skilled in the art can practice the present invention to its fullest extent. The following detailed examples further describe how to use clindamycin and primaquine or salts thereof to treat patients with *Pneumocystis carinii* pneumonia or immunosuppressed patients susceptible to developing *Pneumocystis carinii* pneumonia. These examples are merely illustrative and are not limitations of the preceding disclosure. Those skilled in the art will promptly recognize appropriate variations from the examples.

EXAMPLE 1

Clindamycin Capsules

One thousand two-piece hard gelatin capsules for oral use, each capsule containing 150 mg of clindamycin hydrochloride, are prepared from the following:

| Clindamycin hydrochloride | 50 gm |
|---|---|
| Lactose | 100 gm |
| Cornstarch | 20 gm |
| Talc | 20 gm |
| Magnesium Stearate | 2 gm |

The clindamycin hydrochloride is added to the other ingredients, mixed and encapsulated in the usual manner.

EXAMPLE 2

Primaqine Capsules

One thousand two-piece hard gelatin capsules for oral use, each capsule containing 50 mg of primaquine phosphate, are prepared from the following:

| Primaquine phosphate | 50 gm |
|---|---|
| Lactose | 100 gm |
| Cornstarch | 20 gm |
| Talc | 20 gm |
| Magnesium Stearate | 2 gm |

The primaquine phosphate is added to the other ingredients, mixed and encapsulated in the usual manner.

EXAMPLE 3

Primaquine Tablets

One thousand tablets, each containing 50 mg of primaquine phosphate, are prepared from the following:

| Primaquine phosphate | 30 gm |
|---|---|
| Lactose | 75 gm |
| Cornstarch | 50 gm |
| Magnesium Stearate | 4 gm |
| Light liquid petrolatum | 5 gm |

The primaquine is added to the other ingredients, mixed and slugged. The slugs are broken down by forcing through a number sixteen screen. The resulting granules are than compressed into tablets.

EXAMPLE 4

Clindamycin and Primaquine Capsules

One thousand two-piece hard gelatin capsules for oral use, each capsule containing 150 mg of clindamycin hydrochloride and 15 mg of primaquine phosphate, are prepared from the following:

| | |
|---|---|
| Clindamycin hydrochloride | 150 gm |
| Primaquine phosphate | 50 gm |
| Lactose | 100 gm |
| Cornstarch | 20 gm |
| Talc | 20 gm |
| Magnesium Stearate | 2 gm |

The clindamycin hydrochloride and primaquine phosphate are added to the other ingredients, mixed and encapsulated in the usual manner.

EXAMPLE 5

Injectable Intravenous Solution

A sterile aqueous solution for parenteral intravenous injection containing 450 mg of clindamycin phosphate and 30 of primaquine phosphate in one liter of solution is prepared from the following:

| | |
|---|---|
| Clindamycin phosphate | 450 mg |
| Primaquine phosphate | 30 mg |
| Water for injection, qs | 1000 mg |

The clindamycin phosphate and primaquine phosphate are sterilized, added to the sterile water, filled into sterile containers and sealed.

We claim:

1. A method of treating or preventing Pneumocystis carinii pneumonia in an infected or immunosupressed patient in need thereof which comprises administering an effective amount of clindamycin and primaquine or pharmaceutical salts thereof to said patient.

2. A method according to claim 1 which comprises treating Pneumocystis pneumonia in an infected patient.

3. A method according to claim 1 which comprises preventing Pneumocystis pneumonia in an immunosupressed patient.

4. A method according to claim 1 where the patient is an human infected with one or more than one strain of a human immunodeficiency virus.

5. A method according to claim 4 where the human is infected with human immunodeficiency virus type I.

6. A method according to claim 4 where the human is infected with human immunodeficiency virus type II.

7. A method according to claim 1 where the administration is oral.

8. A method according to claim 1 where the effective amount is from about 0.1 to 100 mg per kg per day of clindamycin and from about 0.1 to 100 mg per kg per day of primaquine.

9. A method according to claim 1 where the administration is parenteral.

10. A method according to claim 9 where the administration is by injection.

11. A method according to claim 9 where the administration is by intravenous fusion.

12. A pharmaceutical composition comprising an effective amount of clindamycin and primaquine or pharmaceutical salts thereof.

13. A composition according to claim 12 useful in treating or preventing *Pneumocystis carinii* pneumonia in an infected or immunosuppressed patient.

14. A composition according to claim 12 wherein an effective amount is from about 0.1 to 100 mg per kg per day of clindamycin and from about 0.1 to 100 mg per kg per day of primaquine.

15. A composition according to claim 12 wherein an effective amount is from about 300 to 1200 mg of clindamycin and from about 1 to 30 mg of primaquine.

* * * * *